United States Patent [19]

Matsui et al.

[11] Patent Number: 4,845,232

[45] Date of Patent: Jul. 4, 1989

[54] PROCESS FOR PRODUCING 1,2,4-TRIAZOLIN-5-ONE DERIVATIVES, AND INTERMEDIATES THEREFOR

[75] Inventors: Hisanori Matsui, Kawaguchi; Keiji Sutoh, Nishinomiya; Moriharu Yamamoto, Kobe; Kazuhiro Takagi, Nishinomiya; Kunihiro Yabutani; Kuniaki Taninaka, both of Neyagawa; Mitsuru Kajioka, Sakai, all of Japan

[73] Assignee: Nihon Nohyaku Co., Ltd., Tokyo, Japan

[21] Appl. No.: 923,935

[22] Filed: Oct. 24, 1986

[30] Foreign Application Priority Data

Oct. 26, 1985 [JP] Japan .................... 60-239998
Mar. 29, 1986 [JP] Japan .................... 61-71942
Apr. 18, 1986 [JP] Japan .................... 61-89672

[51] Int. Cl.$^4$ .................................. C07D 249/12
[52] U.S. Cl. ............................ 548/265; 548/263; 548/264
[58] Field of Search ................ 548/263, 264, 265

[56] References Cited

U.S. PATENT DOCUMENTS 4,318,731  3/1982  Kajioka et al. .............. 71/92
4,398,943  7/1983  Kajioka et al. .............. 71/92

FOREIGN PATENT DOCUMENTS 0055105   6/1982  European Pat. Off. ........... 71/92
3514057   5/1985  Fed. Rep. of Germany ....... 71/92
3426634   7/1985  Fed. Rep. of Germany.
181069   11/1982  Japan ........................ 548/265
6048977   3/1985  Japan ........................ 548/265
6051180   3/1985  Japan ........................ 548/265
8501637   4/1985  PCT Int'l Appl. ............. 71/92
8504307  10/1985  PCT Int'l Appl. ............. 71/92

OTHER PUBLICATIONS

Publication: Preparative Organic Chemistry, Edited by G. Hilgetag and A. Martini, pp. 152–159.

European Search Report, EP86308284.8, 1/11/87.
PCT Patent Application No. WO86/02642, Maravetz I.

Primary Examiner—Richard L. Raymond
Assistant Examiner—Patricia L. Morris
Attorney, Agent, or Firm—Cushman, Darby & Cushman

[57] ABSTRACT

A process for producing 1,2,4-triazolin-5-one derivatives represented by the general formula (I)

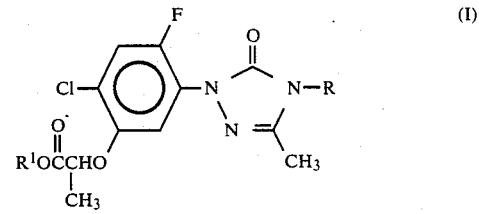

wherein R is a haloalkyl group of 1 to 5 carbon atoms and $R^1$ is a hydrogen atom, an alkyl group of 1 to 6 carbon atoms, an alkyl group of 1 to 6 carbon atoms having halogen atom substituents, a cycloalkyl group of 3 to 6 carbon atoms, a cycloalkyl group of 3 to 6 carbon atoms having halogen atom substituents, a cyanoalkyl group of 2 to 4 carbon atoms, an alkenyl group of w to 6 carbon atoms, an alkynyl group of 2 to 6 carbon atoms, a lower alkoxyalkyl group of 2 to 6 carbon atoms, a lower alkylthioalkyl group of 2 to 8 carbon atoms, a lower alkylsufinylalkyl group of 2 to 6 carbon atoms, a lower alkylsufonylalkyl group of 2 to 6 carbon atoms, a lower alkoxyalkoxyalkyl group of 3 to 8 carbon atoms, a hydroxycarbonylalkyl group of 2 to 3 carbon atoms, a lower alkoxycarbonylalkyl group of 3 to 6 carbon atoms, a benzylgroup, a benzyl group having 1 to 2 substituents (selected from a halogen atom, a lower alkyl group of 1 to 3 carbon atoms, a lower alkoxy group of 1 to 3 carbon atoms, a nitro group, a lower alkoxycarbonyl group of 2 to 4 carbon atoms, a hydroxycarbonyl group and a phenoxy group), an alpha-methylbenzyl group or a phenethyl group.

15 Claims, No Drawings

PROCESS FOR PRODUCING 1,2,4-TRIAZOLIN-5-ONE DERIVATIVES, AND INTERMEDIATES THEREFOR

BACKGROUND OF THE INVENTION

1. Field of the Invention

This invention relates to a process for producing triazoline derivatives. More particularly, the present invention relates to a process for producing N-(2-fluorine-substituted-phenyl)thiazoline derivatives represented by the general formula (I)

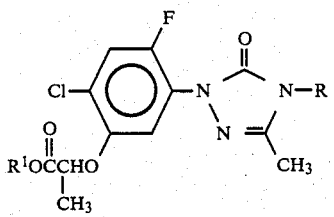

[wherein R is a haloalkyl group of 1 to 5 carbon atoms and $R^1$ is a hydrogen atom, an alkyl group of 1 to 6 carbon atoms, an alkyl group of 1 to 6 carbon atoms having halogen atom substituents, a cycloalkyl group of 3 to 6 carbon atoms, a cycloalkyl group of 3 to 6 carbon atoms having halogen atom substituents, a cyanoalkyl group of 2 to 4 carbon atoms, an alkenyl group of 2 to 6 carbon atoms, an alkynyl group of 2 to 6 carbon atoms, a lower alkoxyalkyl group of 2 to 6 carbon atoms, a lower alkylthioalkyl group of 2 to 8 carbon atoms, a lower alkylsulfinylalkyl group of 2 to 6 carbon atoms, a lower alkylsulfonylalkyl group of 2 to 6 carbon atoms, a lower alkoxyalkoxyalkyl group of 3 to 8 carbon atoms, a hydroxycarbonylalkyl group of 2 to 3 carbon atoms, a lower alkoxycarbonylalkyl group of 3 to 6 carbon atoms, a benzyl group, a benzyl group having 1 to 2 substituents (selected from a halogen atom, a lower alkyl group of 1 to 3 carbon atoms, a lower alkoxy group of 1 to 3 carbon atoms, a nitro group, a lower alkoxycarbonyl group of 2 to 4 carbon atoms, a hydroxycarbonyl group and a phenoxy group), an alpha-methylbenzyl group or a phenethyl group], and provides a process for producing such compounds useful as an agricultural chemical, particularly as a herbicide, as well as processes for producing intermediates for said compounds.

The compounds produced according to the process of the present invention are useful as a herbicide particularly for soybean, as mentioned in U.S. Patent Application Nos. 712,233 and 845,867 and W086/02642.

2. Related Art

Processes for producing triazoline derivatives are disclosed in U.S. Pat. Nos. 4,318,731 and 4,398,943, W086/02642, etc. However, these processes are not preferable for industrial application because they employ many steps and use, as one starting material, an expensive substituted phenylhydrazine wherein the 2-position of the phenyl ring has a fluorine atom substituent.

OBJECT AND SUMMARY OF THE INVENTION

The present inventors made an extensive study to solve the above mentioned problems of the conventional processes for producing triazoline derivatives. As a result, the present invention has been completed.

In the general formula (I), as the substituent R, there can be mentioned, for example, haloalkyl groups such as difluoromethyl, trifluoromethyl, 2-chloro-1,1,2-trifluoroethyl, 1,1,2,2-tetrafluoroethyl, 2,2,2-trifluoroethyl, 3-chloropropyl, 3-bromopropyl, 3-fluoropropyl, 2,2-difluoropropyl, 1,1,2,3,3,3-hexafluoropropyl, 4-chlorobutyl, 4-fluorobutyl, 5-chloropentyl, 5-fluoropentyl and the like. The substituent R is particularly preferably difluoromethyl and 1,1,2,2-tetrafluoroethyl.

As the substituent $R^1$, there can be mentioned, for example, a hydrogen atom; alkyl groups such as methyl, ethyl, n-propyl, isopropyl, n-butyl, isobutyl, s-butyl, t-butyl, pentyl, hexyl and the like; alkyl groups having halogen atom substituents such as chloromethyl, bromomethyl, chloroethyl, bromoethyl, chloropropyl, bromopropyl, chlorobutyl, bromobutyl, chloropentyl, bromopentyl, chlorohexyl, bromohexyl and the like; cycloalkyl groups such as cyclopropyl, cyclopentyl, cyclohexyl and the like; cycloalkyl groups having halogen atom substituents such as 2-chlorocyclopentyl, 2-chlorocyclohexyl and the like; alkenyl groups such as ethenyl, 2-propenyl, 1-methylpropenyl, 1,1-dimethylpropenyl, 2-butenyl, pentenyl, hexenyl and the like; alkynyl groups such as ethynyl, 2-propynyl, 1-methylpropynyl, 1,1-dimethylpropynyl, 2-butynyl, pentynyl, hexynyl and the like; alkoxyalkyl groups such as methoxymethyl, ethoxymethyl, propoxymethyl, butoxymethyl, pentyloxymethyl, methoxyethyl, ethoxyethyl, propoxyethyl, butoxyethyl, methoxypropyl, ethoxypropyl, propoxypropyl, methoxybutyl, ethoxybutyl, methoxypentyl and the like; alkylthioalkyl groups such as methylthiomethyl, ethylthiomethyl, propylthiomethyl, butylthiomethyl, pentylthiomethyl, hexylthiomethyl, methylthioethyl, ethylthioethyl, propiothioethyl, butylthioethyl, methylthiopropyl, ethylthiopropyl, propylthiopropyl and the like; alkylsulfinylalkyl groups such as methylsulfinylmethyl, methylsulfinylethyl and the like; alkylsulfonylalkyl groups such as methylsulfonylmethyl, methylsulfonylethyl and the like; alkoxyalkoxyalkyl groups such as methoxymethoxymethyl, ethoxymethoxymethyl, propoxymethoxymethyl, butoxymethoxymethyl, methoxyethoxyethyl, ethoxyethoxyethyl and the like; hydroxycarbonylalkyl groups such as hydroxycarbonylmethyl, hydroxycarbonylethyl and the like; alkoxycarbonylalkyl groups such as methoxycarbonylmethyl, ethoxycarbonylethyl and the like; a benzyl group; benzyl groups having 1 to 2 substituents selected from a halogen atom, a lower alkyl group of 1 to 3 carbon atoms, a lower alkoxy group of 1 to 3 carbon atoms, a nitro group, a lower alkoxycarbonyl group of 2 to 4 carbon atoms, a hydroxycarbonyl group and a phenoxy group; an alpha-methylbenzyl group; and a phenethyl group. The substituent $R^1$ is preferably a hydrogen atom, a methyl group, an ethyl group, a propyl group, a 2-chloroethyl group, a 3-chloropropyl group, a 4-chlorobutyl group, a 2-propenyl group, a 2-propynyl group, a methoxyethyl group, an ethoxyethyl group and a methoxyethoxyethyl group.

The production process of the present invention consists of three steps and can be illustrated by the following diagram.

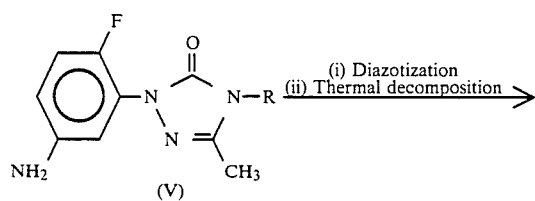

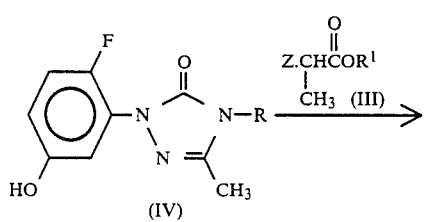

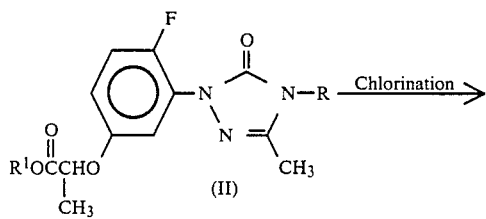

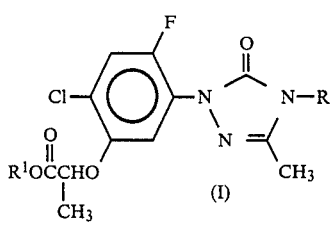

(wherein R and R¹ have each the same definition as given previously and Z is a halogen atom.)

The compound represented by the general formula (V) can be produced according to a process shown by the following diagram.

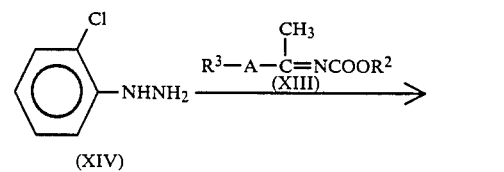

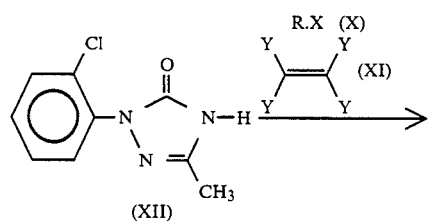

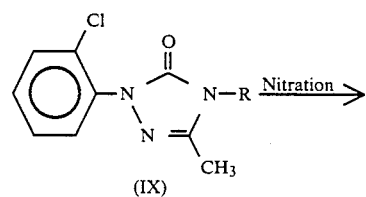

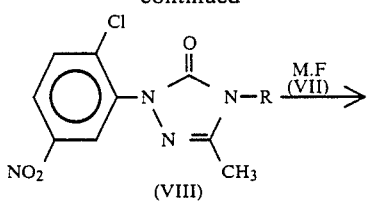

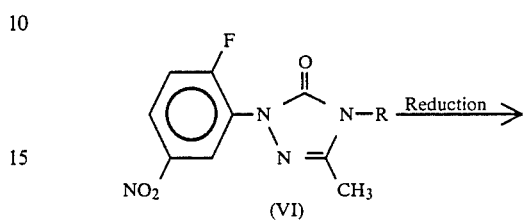

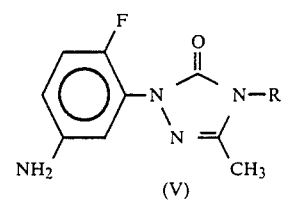

(wherein R has the same definition as given previously; R² and R³ are each a lower alkyl group; A is an oxygen atom or a sulfur atom; X and Y may be same or different and are each a halogen atom; and M is an alkali metal atom.)

DETAILED DESCRIPTION OF PREFERRED EMBODIMENTS

The compound represented by the general formula (V) can specifically be produced as follows. That is, a hydrazine represented by the general formula (XIV) and a compound represented by the general formula (XIII) are reacted in the presence of a solvent and then subjected to a ring closure reaction in the presence of a base to obtain a compound represented by the general formula (XII); said compound (XII) and a compound represented by the general formula (X) or (XI) are reacted in the presence of a base to obtain a compound represented by the general formula (IX); said compound (IX) is nitrated to obtain a compound represented by the general formula (VIII); said compound (VIII) and a compound represented by the general formula (VII) are reacted to obtain a compound represented by the general formula (VI); and said compound (VI) is reduced to obtain a compound represented by the general formula (V). Examples of synthesis of the compound (V) will be described below by way of Reference Examples.

Reference Example (a) Production of 1-(2-chlorophenyl)-3-methyl-Δ²-1,2,4-triazolin-5-one

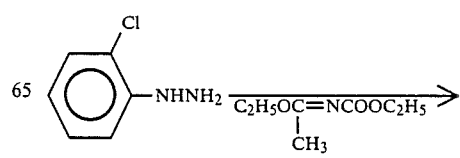

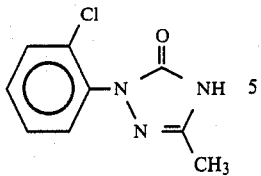

100 g (0.7 mole) of 2-chlorophenylhydrazine was dissolved in 800 ml of xylene. Thereto was added 122.4 g (0.77 mole) of ethyl N-[(1-ethoxy)ethylidene]-carbamate, and they were subjected to reaction for 1 hour and 30 minutes at 40° to 50° C. Then, 77.9 g (0.77 mole) of triethylamine was added and the whole mixture was refluxed with heating, for 12 hours. After the completion of the reaction, the reaction mixture was cooled to room temperature and subjected to vacuum distillation to remove the solvent and excessive triethylamine, whereby the captioned compound was obtained. Melting point: 176.9° C. Yield: 95%

Reference Example (b) Production of 1-(2-chlorophenyl)-3-methyl-4-(1,1,2,2-tetrafluoroethyl)-Δ²-1,2,4-triazolin-5-one

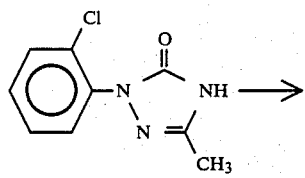

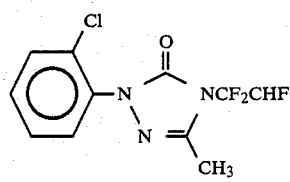

38.2 g (0.28 mole) of 1-(2-chlorophenyl)-3-methyl-Δ²-1,2,4-triazolin-5-one was dissolved in 250 ml of dimethylformamide. Thereto was added 18.5 g (0.28 mole) of a powder of potassium hydroxide, and they were heated to 110° C. Thereto was introduced 27 g (0.27 mole) of tetrafluoroethylene over 4 hours. After the completion of the introduction, the whole mixture was stirred with heating, for 1.5 hours. After the completion of the reaction, the reaction mixture was cooled and poured into ice water. Extraction with ethyl acetate was conducted and the extract was water-washed, dried and then subjected to vacuum distillation to remove ethyl acetate, whereby 55.72 g of the captioned compound was obtained. Melting point: 47.8° C. Yield: 100%

Reference Example (c) Production of 1-(2-chloro-5-nitrophenyl)-3-methyl-4-(1,1,2,2-tetrafluoroethyl)-Δ²-1,2,4-triazolin-5-one

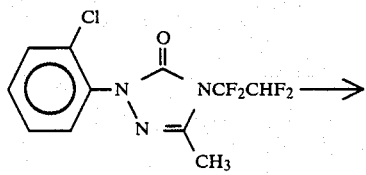

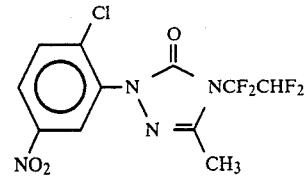

58.4 g (0.19 mole) of 1-(2-chlorophenyl)-3-methyl-(1,1,2,2-tetrafluoroethyl)-Δ²-1,2,4-triazolin-5-one was dissolved in 300 ml of concentrated sulfuric acid. Thereto was dropwise added a mixture consisting of 33.5 ml of 60% nitric acid and 125 ml of concentrated sulfuric acid, at 0° C. or below. After the completion of the dropping, the mixture was stirred for 1 hour and the reaction mixture was poured into ice water. Extraction with ethyl acetate was conducted. The extract was waterwashed, dried and then subjected to vacuum distillation to remove ethyl acetate. The resulting crystal was recrystallized to obtain 56.19 g of the captioned compound. Melting point: 111.7° C. Yield: 84%

Reference Example (d) Production of 1-(2-fluoro-5-nitrophenyl)-3-methyl-4-(1,1,2,2-tetrafluoroethyl)-Δ²-1,2,4-triazolin-5-one

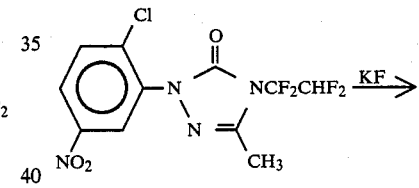

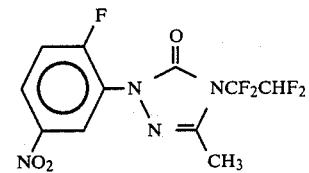

A mixture of 3.0 g (0.0085 mole) of 1-(2-chloro-5-nitrophenyl)-3-methyl-4-(1,1,2,2-tetrafluoroethyl)-Δ²-1,2,4-triazolin-5-one, 0.59 g (0.0102 mole) of anhydrous potassium fluoride and 50 ml of dimethylsulfone was stirred for 1 hour at 200° C. for reaction. After the completion of the reaction, the reaction mixture was cooled to room temperature and poured into ice water. Extraction with ethyl acetate was conducted. The extract was water-washed, dried and subjected to vacuum distillation to remove the solvent, whereby an oily substance was obtained. This oily substance was allowed to stand at room temperature, whereby a crystal was formed. The crystal was recrystallized to obtain 2.44 g of the captioned compound. Melting point: 80.7° C. Yield: 85%

Reference Example (e) Production of 1-(5-amino-2-fluorophenyl)-3-methyl-4-(1,1,2,2-tetrafluoroethyl)-Δ²-1,2,4-triazolin-5-one

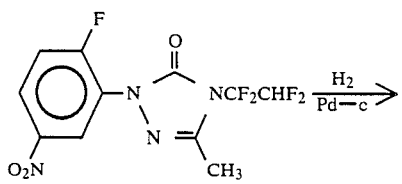

1.41 g (0.0042 mole) of 1-(2-fluoro-5-nitrophenyl)-3-methyl-4-(1,1,2,2-tetrafluoroethyl)-Δ²-1,2,4-triazolin-5-one was dissolved in 100 ml of tetrahydrofuran. Thereto was added 1.4 g of 5% palladium-on-carbon, and hydrogen gas was passed therethrough for 4 hours at room temperature. After the completion of of the reaction, the catalyst was removed by filtration and the extract was subjected to vacuum distillation to remove the solvent, whereby a crystal was formed. The crystal was recrystallized from ethanol-water to obtain 1.11 g of the captioned compound. Melting point: 98.6° C. Yield: 86%

The first step of the production process of the present invention is conducted according to the following diagram

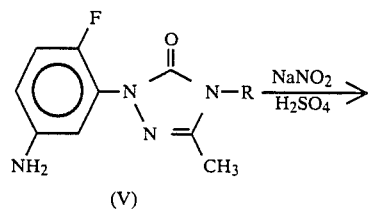
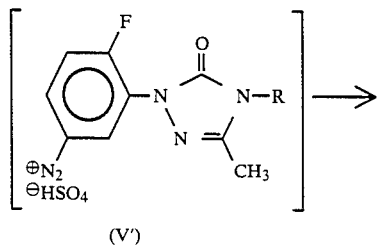
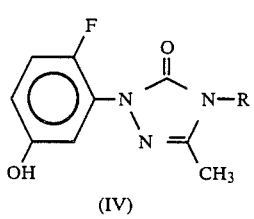

(wherein R has the same definition as given previously). That is, a compound represented by the general formula (V) is subjected to diazotization according to an ordinary method, for example, with sodium nitrite in an aqueous sulfuric acid solution to convert to a compound represented by the general formula (V'); then, said compound (V') is subjected to thermal decomposition without isolating it, whereby a triazolin-5-one derivative represented by the general formula (IV) can be obtained.

The reaction temperature of the above reaction can be 5° C. or lower for diazotization and can be appropriately selected from room temperature to 250° C. for thermal decomposition.

The reaction time can be appropriately selected from 0.5 to 6 hours.

With respect to the amounts of the raw materials used in the above reaction, sodium nitrite and sulfuric acid can be appropriately selected from 1.0 to 2.0 moles and 1.5 to 50 moles, respectively, based on 1 mole of the compound represented by the general formula (V). When the diazotization reaction is conducted, for example, in an aqueous sulfuric acid solution, ordinarily it is not necessary to supplement water in the subsequent thermal decomposition; however, water can be supplemented as necessary in the thermal decomposition in order to obtain an intended product of high purity.

After the completion of the reaction, extraction with ethyl acetate or the like is conducted and the extract is dried and then subjected to distillation to remove the extraction solvent, whereby a triazolin-5-one derivative represented by the general formula (IV) can be obtained.

Typical examples of the compound of the general formula (IV) produced according to the first step are shown in Table 1.

TABLE 1

| Compound No. | R | Physical properties |
|---|---|---|
| IV-1 | $CHF_2$ | M.p. 115.5° C. |
| IV-2 | $CHF_2CF_2$ | M.p. 135.2° C. |

The first step will be explained by way of Example.

Example 1 Production of 1-(2-fluoro-5-hydroxyphenyl)-3-methyl-4-(1,1,2,2-tetrafluoroethyl)-Δ²-1,2,4-triazolin-5-one (compound No. IV-2)

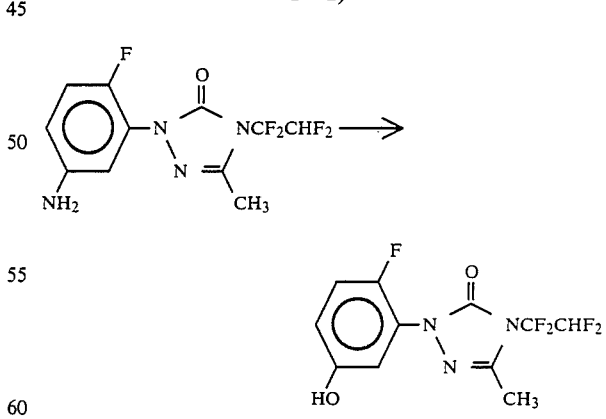

1.5 g (0.0049 mole) of 1-(5-amino-2-fluorophenyl)-3-methyl-4-(1,1,2,2-tetrafluoroethyl)-Δ²-1,2,4-triazolin-5-one was dissolved in 10 ml of 50% (volume) sulfuric acid. Thereto was dropwise added a solution of 0.34 g (0.0049 mole) of sodium nitrite dissolved in 1 ml of water, with ice-cooling, whereby a diazonium salt was synthesized.

The above reaction mixture containing said diazonium salt was added to 80 ml of 50% sulfuric acid heated to 150° C., and reaction was conducted to the termination of foaming. The reaction mixture was cooled and then poured into ice water. Extraction with dichloromethane was conducted. The extract was waterwashed, dried and subjected to distillation to remove dichloromethane, whereby 1.24 g of the captioned compound was obtained. Melting point: 135.2° C. Yield: 82.1%

The second step of the production process of the present invention can be illustrated by the following diagram

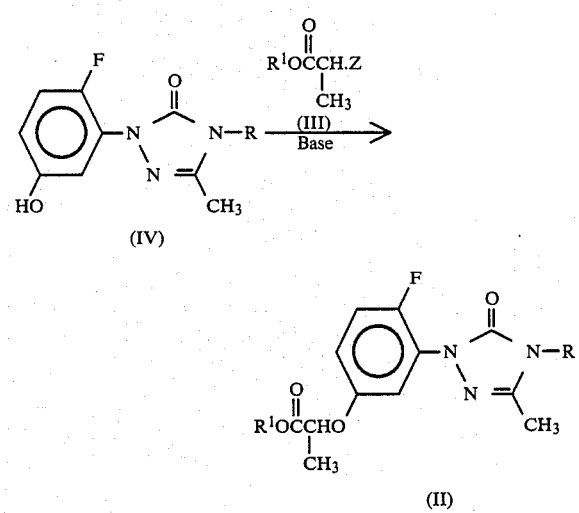

(wherein R and $R^1$ have each the same definition as given previously and Z is a halogen atom).

In the second step, the compound of the general formula (IV) obtained in the first step is reacted with a compound represented by the general formula (III) in an inert solvent in the presence of a base, to obtain a compound represented by the general formula (II). The inert solvent can be any solvent unless it significantly hinders the progress of the above reaction. The inert solvent can be, for example, aromatic hydrocarbons such as benzene, toluene, xylene and the like; aliphatic hydrocarbons such as n-hexane, cyclohexane and the like; alcohols such as methanol, ethanol, propanol, glycol and the like; ketones such as acetone, methyl ethyl ketone, cyclohexanone and the like; lower fatty acid esters such as ethyl acetate and the like; ethers such as tetrahydrofuran, dioxane and the like; lower fatty acid amides such as dimethylformamide, dimethylacetamide and the like; cyanoalkanes such as acetonitrile and the like; water; and dimethyl sulfoxide.

These solvents can be used singly or as a mixture of two or more. As the base used in the above reaction, there can be mentioned, for example, inorganic bases such as sodium carbonate, sodium hydride, potassium carbonate, sodium hydrogencarbonate, potassium hydrogen carbonate, sodium hydroxide, potassium hydroxide, alkali metal alcoholates and the like, as well as organic bases such as pyridine, trimethylamine, triethylamine, diethylaniline, 1,8-diazabicyclo-[5,4,0]-7-undecene and the like.

The reaction of the second step can be effected ordinarily under heating, for example, at a temperature appropriately selected from 50° to 150° C.

The reaction is an equimolar reaction but either of the reactants can be used at a slight excess.

The reaction time can be selected from 0.5 to 48 hours.

After the completion of the reaction, the reaction mixture is treated according to an ordinary manner, whereby an intended compound represented by the general formula (II) can be collected.

Typical examples of the compound of the general formula (II) are shown in Table 2.

TABLE 2

| Compound No. | R | $R^1$ | Physical properties |
|---|---|---|---|
| II-1 | $CHF_2$ | H | Oily substance |
| II-2 | $CHF_2$ | $C_2H_5$ | $n_D^{22}$ 1.5032 |
| II-3 | $CHF_3$ | $Cl(CH_2)_3$ | $n_D^{25.5}$ 1.5107 |
| II-4 | $CHF_2$ | $CH_2=CHCH_2$ | $n_D^{22}$ 1.5103 |
| II-5 | $CHF_2CF_2$ | H | Oily substance |
| II-6 | $CHF_2CF_2$ | $C_2H_5$ | $n_D^{20}$ 1.4798 |
| II-7 | $CHF_2CF_2$ | $Cl(CH_2)_3$ | $n_D^{20}$ 1.4879 |
| II-8 | $CHF_2CF_2$ | ⟨cyclohexyl-H⟩ | $n_D^{25}$ 1.4907 |
| II-9 | $CHF_2CF_2$ | $CH_2=CHCH_2$ | $n_D^{25}$ 1.4890 |
| II-10 | $CHF_2CF_2$ | $CH\equiv CCH_2$ | $n_D^{25.5}$ 1.4933 |
| II-11 | $CHF_2CF_2$ | $CH_3O(CH_2)_2$ | $n_D^{22}$ 1.4792 |
| II-12 | $CHF_2CF_2$ | $t-C_4H_9S(CH_2)_2$ | $n_D^{25.5}$ 1.4958 |
| II-13 | $CHF_2CF_2$ | $CH_3O(CH_2)_2O(CH_2)_2$ | $n_D^{20}$ 1.4769 |
| II-14 | $CHF_2CF_2$ | ⟨phenyl⟩-$CH_2$ | $n_D^{25.5}$ 1.5169 |

For those compounds of Table 2 which are oily substances, their NMR data are shown in Table 3.

TABLE 3

| Compound No. | $NMR^{CDCl_3}_{TMS}$ (ppm) |
|---|---|
| II-1 | 1.60(d, 3H), 2.40(s, 3H), 4.70(q, 1H), 7.05(t, 1H), 6.7–7.2(m, 3H), 9.20(s, 1H) |
| II-5 | 1.60(d, 3H), 2.40(t, 3H), 4.70(t, 1H), 6.85(t, t, 1H), 6.7–7.2(m, 3H), 10.0(s, 1H) |

Example 2 Production of
4-difluoromethyl-1-[5-{1-(ethoxycarbonyl)ethoxy}-2-fluorophenyl]-3-methyl-Δ²-1,2,4-triazolin-5-one
(compound II-2)

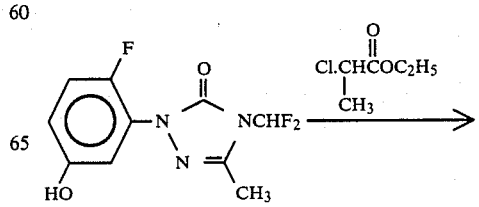

-continued

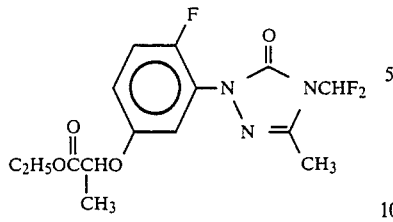

2.59 g (0.01 mole) of 4-difluoromethyl-1-(2-fluoro-5-hydroxyphenyl)-3-methyl-Δ²-1,2,4-triazolin-5-one obtained in the same manner as in Example 1 was reacted with a mixture of 1.50 g (0.011 mole) of ethyl alpha-chloropropionate, 2.0 g (0.014 mole) of anhydrous potassium carbonate and 50 ml of dimethyl sulfoxide, for 1 hour at 130° C. After the completion of the reaction, the reaction mixture was cooled to room temperature and poured into ice water. Extraction with ethyl acetate was conducted. The extracted was water-washed, dried and then subjected to vacuum distillation to remove ethyl acetate, whereby 3.23 g of the captioned compound was obtained. $n_D^{22}$: 1.5032 Yield: 90%

Example 3 Production of 1-[5-{1-(3-chloropropyloxycarbonyl)ethoxy}-2-fluorophenyl]-4-difluoromethoxy-3-methyl-Δ²-1,2,4-triazolin-5-one (compound II-3)

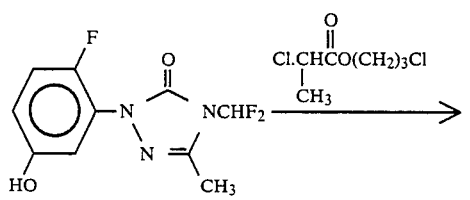

2.59 g (0.01 mole) of 4-difluoromethyl-1-(2-fluoro-5-hydroxyphenyl)-3-methyl-Δ²-1,2,4-triazolin-5-one obtained in the same manner as in Example 1 was reacted with a mixture of 2.04 g (0.011 mole) of 3-chloropropyl alphachloropropionate, 2.0 g (0.014 mole) of anhydrous potassium carbonate and 50 ml of acetonitrile, for 5 hours at 70° C. After the completion of the reaction, the reaction mixture was cooled to room temperature and poured into ice water. Extraction with ethyl acetate was conducted. The extract was water-washed, dried and then subjected to vacuum distillation to remove ethyl acetate, whereby 3.46 g of the captioned compound was obtained. $n_D^{25.5}$: 1.5107 Yield: 85%

Example 4 Production of 1-[5-{1-(3-chloropropyloxycarbonyl)ethoxy}-2-fluorophenyl]-4-(1,1,2,2-tetrafluoroethyl)-3-methyl-Δ²-1,2,4-triazolin-5-one (compound II-7)

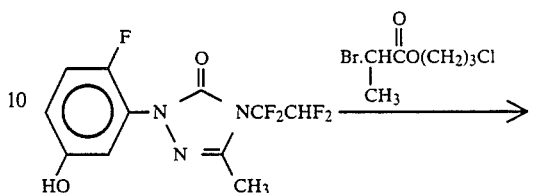

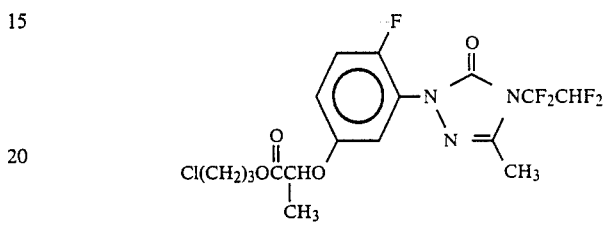

A mixture of 1.0 g (0.0032 mole) of 1-(2-fluoro-5-hydroxyphenyl)-3-methyl-4-(1,1,2,2-tetrafluoroethyl)-Δ²-1,2,4-triazolin-5-one obtained in Example 1, 0.82 g (0.0036 mole) of 3-chloropropyl alpha-bromopropinate, 0.89 g (0.0064 mole) of anhydrous potassium carbonate and 40 ml of acetone was refluxed for 2 hours with heating and stirring. After the completion of the reaction, the reaction mixture was cooled to room temperature. Then, the insolubles were removed by filtration and acetone was removed by vacuum distillation, whereby 1.46 g of the captioned compound was obtained. $n_D^{22}$: 1.4879 Yield: 100%

Example 5 Production of 1-[5-{1-(benzyloxycarbonyl)ethoxy}-2-fluorophenyl]-3-methyl-4-(1,1,2,2-tetrafluoroethyl)-Δ²-1,2,4-triazolin-5-one (compound II-14)

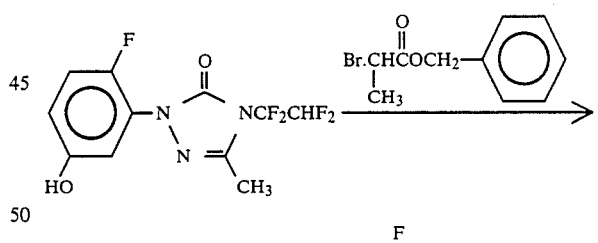

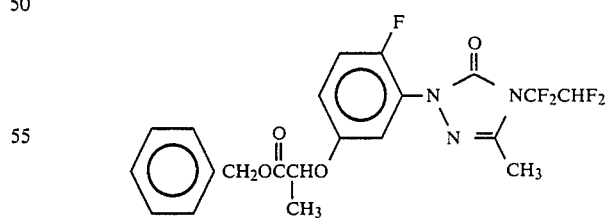

3.09 g (0.01 mole) of 1-(2-fluoro-5-hydroxyphenyl)-3-methyl-4-(1,1,2,2-tetrafluoroethyl)-Δ²-1,2,4-triazolin-5-one obtained in Example 1 was dissolved in 50 ml of dimethylformamide. The resulting solution was dropwise added to a suspension consisting of 0.44 g (0.011 mole) of 60% NaH and 20 ml of dimethylformamide. The mixture was stirred for 30 minutes. Thereto was added 2.67 g (0.011 mole) of benzyl alpha-bromopropionate, and the whole mixture was subjected to reaction for 2 hours at 50° to 60° C. After the completion of the reaction, the reaction mixture was cooled to room temperature and poured into ice water. Extraction with ethyl acetate was conducted. The extract was water-washed, dried and then subjected to vacuum distillation to remove ethyl acetate, whereby 4.2 g of the captioned compound was obtained. $n_D^{25.5}$: 1.5169 Yield: 89.4%

The third step of the production process of the present invention can be illustrated by the following diagram.

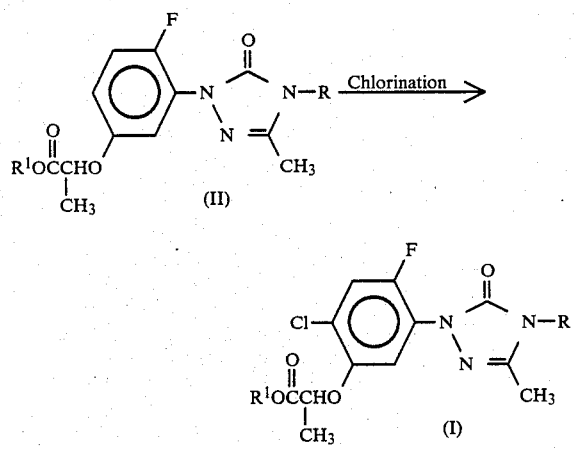

(wherein R and $R^1$ have each the same definition as given previously). In the third step, the compound of the general formula (II) obtained in the second step is reacted with a chlorinating agent in an inert solvent, whereby a compound represented by the general formula (I) can be obtained.

As the inert solvent usable in the above reaction, there can be mentioned, for example, acetonitrile, carbon tetrachloride, chlorobenzene and acetic acid. Other solvents also can be used as long as they are inert to the chlorination.

As the chlorinating agent usable in the above reaction, there can be mentioned, chlorine, thionyl chloride, sulfuryl chloride, phosphorus oxychloride, phosphorus pentachloride, etc.

The amount of the chlorinating agent used can be appropriately selected from 1.0 to 5.0 moles, based on 1 mole of the compound represented by the general formula (II). The amount is preferably 1.1 to 1.5 moles on the same basis.

The reaction temperature can be selected from 0° to 150° C. The reaction time can be selected from 0.5 to 6 hours.

After the completion of the reaction, the reaction mixture is subjected to solvent extraction; the extract is subjected to distillation to remove the solvent; the resulting crude product is purified by recrystallization or the like, whereby an intended product of the general formula (I) can be obtained.

Typical examples of the compound of the general formula (I) obtained according to the production process of the present invention are shown in Table 4. However, the compounds (I) of the present invention are not restricted to them.

TABLE 4

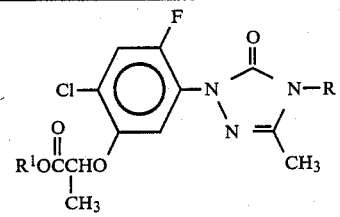

| Compound No. | $R^1$ | R | Physical properties |
|---|---|---|---|
| I-1 | H | $CHF_2$ | $n_D^{24.5}$ 1.5192 |
| I-2 | H | $CF_2CHF_2$ | $n_D^{24}$ 1.5079 |
| I-3 | H | $CH_2CF_3$ | m.p. 180.9° C. |
| I-4 | H | $CF_2CHClF$ | m.p. 107.8° C. |
| I-5 | $CH_3$ | $CHF_2$ | $n_D^{23}$ 1.5142 |
| I-6 | $CH_3$ | $CF_2CHF_2$ | $n_D^{23}$ 1.4977 |
| I-7 | $C_2H_5$ | $CHF_2$ | $n_D^{19}$ 1.5112 |
| I-8 | $C_2H_5$ | $CF_2CHF_2$ | $n_D^{24}$ 1.4891 |
| I-9 | $C_2H_5$ | $CH_2CF_3$ | $n_D^{19.5}$ 1.5030 |
| I-10 | $i-C_3H_7$ | $CHF_2$ | $n_D^{23}$ 1.5051 |
| I-11 | $n-C_4H_9$ | $CHF_2$ | $n_D^{29}$ 1.5031 |
| I-12 | $i-C_4H_9$ | $CHF_2$ | $n_D^{29}$ 1.5011 |
| I-13 | $s-C_4H_9$ | $CF_2CHFCl$ | $n_D^{23}$ 1.4985 |
| I-14 | $t-C_4H_9$ | $CHF_2$ | $n_D^{26}$ 1.5009 |
| I-15 | $n-C_5H_{11}$ | $CHF_2$ | $n_D^{27.5}$ 1.4984 |
| I-16 | $i-C_5H_{11}$ | $CHF_2$ | $n_D^{26}$ 1.5002 |
| I-17 | $n-C_6H_{13}$ | $CHF_2$ | $n_D^{28.5}$ 1.4992 |
| I-18 | $n-C_6H_{13}$ | $CF_2CHF_2$ | $n_D^{26}$ 1.4832 |
| I-19 | $Cl(CH_2)_2$ | $CHF_2$ | $n_D^{26.5}$ 1.5204 |
| I-20 | $Cl(CH_2)_2$ | $CF_2CHF_2$ | $n_D^{18}$ 1.5049 |
| I-21 | $Br(CH_2)_2$ | $CHF_2$ | $n_D^{19.5}$ 1.5291 |
| I-22 | $Br(CH_2)_2$ | $CF_2CHF_2$ | $n_D^{26}$ 1.5092 |
| I-23 | $Br(CH_2)_2$ | $CF_2CHClF$ | $n_D^{23}$ 1.5194 |
| I-24 | $CCl_3CH_2-$ | $CHF_2$ | m.p. 106.5° C. |
| I-25 | $CF_3CH_2-$ | $CHF_2$ | $n_D^{19.5}$ 1.4826 |
| I-26 | $Cl(CH_2)_3$ | $CHF_2$ | m.p. 87.7° C. |

TABLE 4-continued (I)

| Compound No. | R¹ | R | Physical properties |
|---|---|---|---|
| I-27 | ClCH$_2$CH— <br> \|<br>CH$_3$ | CHF$_2$ | m.p. 68.7° C. |
| I-28 | Cl(CH$_2$)$_3$ | CF$_2$CHF$_2$ | m.p. 48.5° C. |
| I-29 | Cl(CH$_2$)$_3$ | CF$_2$CHClF | n$_D^{23}$ 1.5102 |
| I-30 | Cl(CH$_2$)$_3$ | CH$_2$CF$_3$ | m.p. 89.3° C. |
| I-31 | ClCH$_2$CHCH$_2$— <br> \|<br>Cl | CHF$_2$ | m.p. 95.0° C. |
| I-32 | ClCH$_2$\<br>    CH—<br>ClCH$_2$/ | CHF$_2$ | n$_D^{14.5}$ 1.5091 |
| I-33 | Br(CH$_2$)$_3$ | CF$_2$CHF$_2$ | n$_D^{26}$ 1.5088 |
| I-34 | BrCH$_2$\<br>    CH—<br>BrCH$_2$/ | CHF$_2$ | m.p. 104.2° C. |
| I-35 | CF$_3$\<br>    CH—<br>CF$_3$/ | CHF$_2$ | n$_D^{19}$ 1.4573 |
| I-36 | Cl(CH$_2$)$_4$ | CHF$_2$ | m.p. 95.3° C. |
| I-37 | Cl(CH$_2$)$_4$ | CF$_2$CHF$_2$ | n$_D^{18}$ 1.5012 |
| I-38 | Cl(CH$_2$)$_4$ | CF$_2$CHClF | n$_D^{23}$ 1.5089 |
| I-39 |  | CHF$_2$ | n$_D^{26}$ 1.5130 |
| I-40 |  | CF$_2$CHF$_2$ | m.p. 62.5°0 C. |
| I-41 |  | CF$_2$CHClF | n$_D^{22}$ 1.5102 |
| I-42 |  | CHF$_2$ | n$_D^{27.5}$ 1.5140 |
| I-43 |  | CF$_2$CHF$_2$ | n$_D^{26}$ 1.4965 |

TABLE 4-continued (I)

[Structure: 4-chloro-2-fluoro-5-(R¹OC(O)CH(CH₃)O-)phenyl substituted triazolinone with N-R and CH₃ groups]

| Compound No. | R¹ | R | Physical properties |
|---|---|---|---|
| I-44 | cyclohexyl (H) | CH₂CF₃ | $n_D^{19.9}$ 1.5059 |
| I-45 | 2-chlorocyclohexyl (H, Cl) | CHF₂ | $n_D^{17.5}$ 1.7174 |
| I-46 | NCCH₂CH₂ | CF₂CHF₂ | m.p. 83.8° C. |
| I-47 | CH₂=CHCH₂ | CHF₂ | $n_D^{28.5}$ 1.5156 |
| I-48 | CH₂=CHCH₂ | CF₂CHF₂ | $n_D^{26}$ 1.4964 |
| I-49 | CH₂=CHCH₂ | CH₂CF₃ | $n_D^{19.9}$ 1.5122 |
| I-50 | CH≡CCH₂ | CHF₂ | $n_D^{28.5}$ 1.5156 |
| I-51 | CH≡CCH₂ | CF₂CHF₂ | $n_D^{23}$ 1.5025 |
| I-52 | CH≡CCH₂ | CF₂CHClF | $n_D^{22}$ 1.5130 |
| I-53 | CH≡CCH₂CH₂ | CHF₂ | $n_D^{17.5}$ 1.5209 |
| I-54 | CH₃O(CH₂)₂ | CHF₂ | $n_D^{26}$ 1.5088 |
| I-55 | CH₃O(CH₂)₂ | CF₂CHF₂ | $n_D^{19}$ 1.4939 |
| I-56 | C₂H₅O(CH₂)₂ | CHF₂ | $n_D^{26}$ 1.5022 |
| I-57 | C₂H₅O(CH₂)₂ | CF₂CHF₂ | $n_D^{26}$ 1.4875 |
| I-58 | C₂H₅O(CH₂)₂ | CF₂CHClF | $n_D^{22}$ 1.5022 |
| I-59 | i-C₃H₇O(CH₂)₂ | CHF₂ | $n_D^{26}$ 1.4989 |
| I-60 | n-C₄H₉O(CH₂)₂ | CHF₂ | $n_D^{26}$ 1.4878 |
| I-61 | n-C₄H₉O(CH₂)₂ | CF₂CHF₂ | $n_D^{23}$ 1.4849 |
| I-62 | CH₃OCHCH₂CH₂ (CH₃) | CHF₂ | $n_D^{27.5}$ 1.5009 |
| I-63 | CH₃SCH₂ | CHF₂ | $n_D^{18}$ 1.5279 |
| I-64 | CH₃S(CH₂)₂ | CHF₂ | $n_D^{26.5}$ 1.5306 |
| I-65 | CH₃S(CH₂)₂ | CF₂CHF₂ | $n_D^{18}$ 1.5128 |
| I-66 | C₂H₅S(CH₂)₂ | CHF₂ | $n_D^{19.5}$ 1.5274 |
| I-67 | i-C₃H₇S(CH₂)₂— | CHF₂ | $n_D^{19.5}$ 1.5233 |
| I-68 | i-C₄H₉S(CH₂)₂— | CHF₂ | $n_D^{19.5}$ 1.5212 |
| I-69 | i-C₄H₉S(CH₂)₂— | CF₂CHF₂ | $n_D^{25}$ 1.5022 |
| I-70 | s-C₄H₉S(CH₂)₂ | CHF₂ | $n_D^{19.5}$ 1.5219 |
| I-71 | t-C₄H₉S(CH₂)₂ | CHF₂ | $n_D^{22.5}$ 1.5179 |
| I-72 | CH₃S(CH₂)₃ | CHF₂ | $n_D^{19.5}$ 1.5299 |
| I-73 | C₂H₅S(CH₂)₃ | CHF₂ | $n_D^{19.5}$ 1.5203 |
| I-74 | C₂H₅S(CH₂)₃ | CF₂CHF₂ | $n_D^{25}$ 1.5061 |
| I-75 | i-C₃H₇S(CH₂)₃ | CHF₂ | $n_D^{19.5}$ 1.5204 |
| I-76 | n-C₄H₉S(CH₂)₃ | CHF₂ | $n_D^{14.5}$ 1.5216 |
| I-77 | n-C₄H₉S(CH₂)₃ | CF₂CHClF | $n_D^{23}$ 1.5103 |
| I-78 | i-C₄H₉S(CH₂)₃ | CHF₂ | $n_D^{14.5}$ 1.5209 |
| I-79 | t-C₄H₉S(CH₂)₃ | CHF₂ | $n_D^{16.5}$ 1.5172 |
| I-80 | CH₃SO(CH₂)₂ | CHF₂ | m.p. 104.5° C. |
| I-81 | i-C₄H₉SO(CH₂)₂ | CF₂CHF₂ | $n_D^{25}$ 1.5038 |
| I-82 | CH₃SO₂(CH₂)₂ | CHF₂ | m.p. 99.8° C. |
| I-83 | i-C₄H₉SO₂(CH₂)₂ | CF₂CHF₂ | $n_D^{25}$ 1.5022 |
| I-84 | C₂H₅SO₂(CH₂)₃ | CF₂CHF₂ | m.p. 122.3° C. |
| I-85 | CH₃O(CH₂)₂O(CH₂)₂ | CHF₂ | $n_D^{26}$ 1.5052 |
| I-86 | CH₃O(CH₂)₂O(CH₂)₂ | CF₂CHF₂ | $n_D^{24}$ 1.4880 |
| I-87 | CH₃O(CH₂)₂O(CH₂)₂ | CF₂CHClF | $n_D^{22}$ 1.5005 |
| I-88 | CH₃OCCH=C(OCH₃) | CHF₂ | m.p. 108.1° C. |
| I-89 | CH₃OCCH=C(OCH₃) | CF₂CHF₂ | $n_D^{23}$ 1.4918 |

TABLE 4-continued (I)

Structure: 4-chloro-2-fluoro-5-[CH(CH₃)OC(O)OR¹]phenyl group attached to N of a triazinone ring with N—R, C=O, and =C(CH₃).

| Compound No. | R¹ | R | Physical properties |
|---|---|---|---|
| I-90 | CH₃OC(=CH—)OCH₃ (CH₃OCCH—, ‖, OCH₃) | CF₂CHClF | $n_D^{23}$ 1.4989 |
| I-91 | C₆H₅—CH₂— | CHF₂ | m.p. 82.4° C. |
| I-92 | C₆H₅—CH₂— | CF₂CHF₂ | m.p. 91.6° C. |
| I-93 | 2-Cl-C₆H₄—CH₂— | CHF₂ | m.p. 117.5° C. |
| I-94 | 3-Cl-C₆H₄—CH₂— | CHF₂ | m.p. 72.6° C. |
| I-95 | 4-Cl-C₆H₄—CH₂— | CHF₂ | m.p. 73.0° C. |
| I-96 | 4-Cl-C₆H₄—CH₂— | CF₂CHF₂ | $n_D^{18}$ 1.5329 |
| I-97 | 4-Cl-C₆H₄—CH₂— | CF₂CHClF | $n_D^{23}$ 1.5386 |
| I-98 | 2-F-C₆H₄—CH₂— | CHF₂ | m.p. 115.7° C. |
| I-99 | 4-F-C₆H₄—CH₂— | CHF₂ | m.p. 80° C. |
| I-100 | 4-CH₃-C₆H₄—CH₂— | CHF₂ | m.p. 102.8° C. |

TABLE 4-continued (I)

Structure: 4-Cl, 5-(R¹OCOCH(CH₃)O), 2-F-phenyl attached via N-N to a triazolinone ring bearing =C(CH₃)–, C=O, and N–R

| Compound No. | R¹ | R | Physical properties |
|---|---|---|---|
| I-101 | 4-CH₃-C₆H₄-CH₂- | CF₂CHF₂ | $n_D^{26}$ 1.5200 |
| I-102 | 4-CH₃O-C₆H₄-CH₂- | CHF₂ | m.p. 89.4° C. |
| I-103 | 4-NO₂-C₆H₄-CH₂- | CHF₂ | m.p. 126.5° C. |
| I-104 | 4-(CH₃OC(O))-C₆H₄-CH₂- | CHF₂ | m.p. 135.3° C. |
| I-105 | 3-(C₆H₅O)-C₆H₄-CH₂- | CHF₂ | $n_D^{26.0}$ 1.5588 |
| I-106 | 2,4-Cl₂-C₆H₃-CH₂- | CHF₂ | m.p. 163° C. |
| I-107 | 2,6-Cl₂-C₆H₃-CH₂- | CHF₂ | m.p. 114.7° C. |
| I-108 | 3,4-(CH₃O)₂-C₆H₃-CH₂- | CHF₂ | m.p. 96.5° C. |
| I-109 | C₆H₅-CH(CH₃)- | CHF₂ | Oily substance |
| I-110 | C₆H₅-CH₂CH₂- | CHF₂ | Oily substance |

TABLE 4-continued (I) [structure shown: fluorophenyl with Cl, R¹OCCHO(CH₃), and triazolinone with N-R, CH₃]

| Compound No. | R¹ | R | Physical properties |
|---|---|---|---|
| I-111 | –CH₂CH₂–(phenyl) | CF₂CHF₂ | $n_D^{23}$ 1.5203 |

For those compounds of Table 4 which are oily substances, their NMR data are shown in Table 5.

TABLE 5

| Compound No. | $NMR_{TMS}^{CCl_4}$ (ppm) |
|---|---|
| I-109 | 1.32–1.77(m, 6H), 2.30(s, 3H), 4.60(2, 1H), 5.76(q, 1H), 6.86(t, 1H) 6.76–7.31(m, 7H) |
| I-110 | 1.56(d, 3H), 2.35(s, 3H), 2.84(t, 2H), 4.28(t, 2H), 4.59(q, 1H), 6.91(t, 1H), 6.85–7.32(m, 7H) |

Example 6 Production of 1-[4-chloro-5-{1-(3-chloropropyloxycarbonyl)ethoxy}-2-fluorophenyl]-3-methyl-4-(1,1,2,2-tetrafluoroethyl)-Δ²-1,2,4-triazolin-5-one (compound I-28)

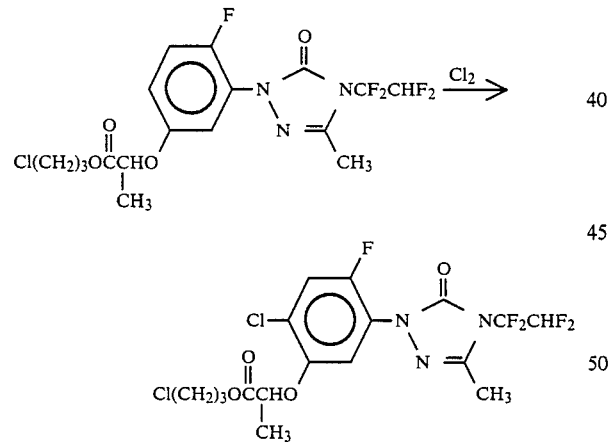

11.5 g (0.02 mole) of 1-[5-{1-(3-chloropropyloxycarbonyl)ethoxy}-2-fluorophenyl]-3-methyl-4-(1,1,2,2-tetrafluoroethyl)-Δ²-1,2,4-triazolin-5-one obtained in Example 4 was dissolved in 150 ml of acetonitrile. Into the resulting solution was introduced chlorine for 2.5 hours at 0° C. After the completion of the reaction, water and ethyl acetate were added to the reaction mixture for extraction. The ethyl acetate layer was separated, water-washed, dried with anhydrous sodium sulfate or the like and then subjected to vacuum distillation to remove the solvent, whereby an oily substance was obtained. The oily substance was allowed to stand for crystallization, whereby 12 g of the captioned compound was obtained in a crystal form. Melting point: 48.5° C. Yield: quantitative

Example 7 Production of 1-[4-chloro-2-fluoro-5-{1-(methoxycarbonyl)ethoxy}phenyl]-4-difluoromethyl-3-methyl-Δ²-1,2,4-triazolin-5-one (compound I-5)

[Reaction scheme: starting material with NCHF₂ group and CH₃OCCHO(CH₃) group undergoes Cl₂ reaction to give product with added Cl on ring]

8.6 g (0.025 mole) of 1-[2-fluoro-5-{1-(methoxycarbonyl)ethoxy}phenyl]-4-difluoromethyl-3-methyl-Δ²-1,2,4-triazolin-5-one obtained in the same manner as in Example 1 was dissolved in 75 ml of acetonitrile. Thereinto was introduced 2.1 g (0.03 mole) of chlorine over 3 hours at 50° C. After the completion of the reaction, the reaction mixture was poured into ice water. Extraction with ethyl acetate was conducted. The extract was dried and subjected to distillation to remove the solvent, whereby an oily substance was obtained. The oily substance was purified according to dry column chromatography to obtain 5.1 g of the captioned compound. $n_D^{23}$: 1.5142 Yield: 54.2%

Example 8 Production of 1-[4-chloro-2-fluoro-5-{1-(ethoxycarbonyl)ethoxy}phenyl]-4-(1,1,2,2-tetrafluoroethyl)-3-methyl-Δ²-1,2,4-triazolin-5-one (compound I-8)

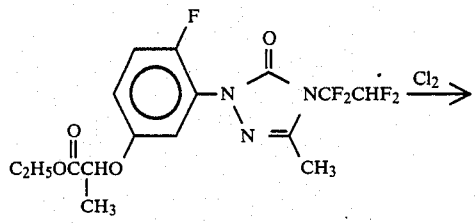

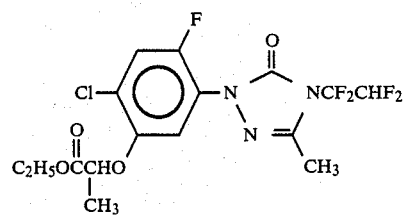

10.2 g (0.025 mole) of 1-[2-fluoro-5-{1-(ethoxycarbonyl)ethoxy}phenyl]-4-(1,1,2,2-tetrafluoroethyl)-3-methyl-Δ²-1,2,4-triazolin-5-one obtained in the same manner as in Example 4 was dissolved in 75 ml of acetonitrile. 3.8 g (0.028 mole) of sulfuryl chloride was dropwise added thereto and reaction was conducted for 4 hours with refluxing. After the completion of the reaction, the reaction mixture was poured into ice water. Extraction with ethyl acetate was conducted. The extract was dried and subjected to distillation to remove the solvent, whereby an oily substance was obtained. The oily substance was purified according to dry column chromatography to obtain 6.9 g of the captioned compound. $n_D^{24}$: 1.4891 Yield: 63%

Example 9

Reaction was conducted in the same manner as in Example 7 except that acetonitrile used in Example 7 was replaced with carbon tetrachloride, whereby an intended compound, namely, 1-[4-chloro-2-fluoro-5-{1-(methoxycarbonyl)ethoxy}phenyl]-4-difluoromethyl-3-methyl-Δ²-1,2,4-triazolin-5-one was obtained at an yield of 58%.

What is claimed is:

1. A process for producing a 1,2,4-triazolin-5-one derivative represented by the general formula (I)

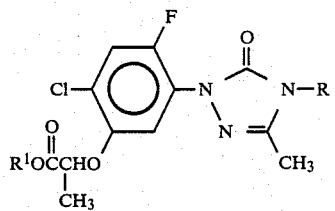

wherein R is a tetrafluoroethyl group and $R^1$ is a hydrogen atom, an alkyl group of 1 to 6 carbon atoms, an alkyl group of 1 to 6 carbon atoms having halogen atom substituents, a cycloalkyl group of 3 to 6 carbon atoms, a cyloalkyl group of 3 to 6 carbon atoms having halogen atom substituents, a cyanoalkyl group of 2 to 4 carbon atoms, an alkenyl group of 2 to 6 carbon atoms, an alkynyl group of 2 to 6 carbon atoms, an alkoxyalkyl group of 2 to 6 carbon atoms, an alkylthioalkyl group of 2 to 8 carbon atoms, an alkylsulfinylalkyl group of 2 to 6 carbon atoms, an alkylsulfonylalkyl group of 2 to 6 carbon atoms, an alkoxyalkoxyalkyl group of 3 to 8 carbon atoms, a hydroxycarbonylalkyl group of 2 to 3 carbon atoms, an alkoxycarbonylalkyl group of 3 to 6 carbon atoms, a benzyl group, a benzyl group having 1 to 2 substituents (selected from a halogen atom, an alkyl group of 1 to 3 carbon atoms, an alkoxy group of 1 to 3 carbon atoms, a nitro group, an alkoxycarbonyl group of 2 to 4 carbon atoms, a hydroxycarbonyl group and a phenoxy group), an alphamethylbenzyl group or a phenethyl group, characterized by subjecting a compound represented by the general formula (V)

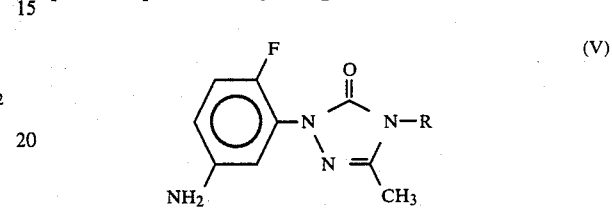

(wherein R has the same definition as given previously) to diazotization and thermal decomposition in this order to obtain a compound represented by the general formula (IV)

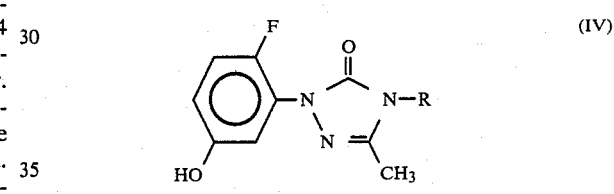

(wherein R has the same definition as given previously), then reacting said compound (IV) with a compound represented by the general formula (III)

(wherein $R^1$ has the same definition as given previously and Z is a halogen atom) to obtain a compound represented by the general formula (II)

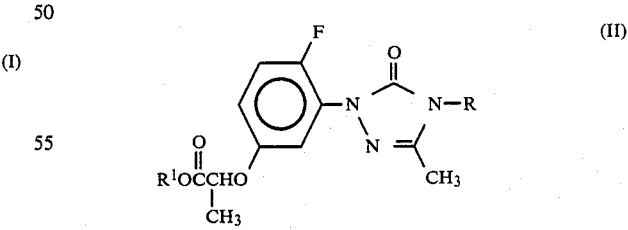

(wherein R and $R^1$ have each the same definition as given previously), and finally chlorinating said compound (II).

2. A process according to claim 1, wherein R is a 1,1,2,2-tetrafluoroethyl group and $R^1$ is a hydrogen atom, an alkyl group of 1 to 6 carbon atoms; an alkyl group of 1 to 6 carbon atoms having a halogen atom substituents, an alkenyl group of 2 to 6 carbon atoms, an alkynyl group of 2 to 6 carbon atoms, an alkoxyalkyl group of 2 to 6 carbon atoms, an alkylthioalkyl group of 2 to 8 carbon atoms or an alkoxyalkoxyalkyl group of 3 to 8 carbon atoms.

3. A process according to claim 2, wherein R is a 1,1,2,2-tetrafluoroethyl group and $R^1$ is a hydrogen atom, an alkyl group of 1 to 6 carbon atoms, an alkyl group of 1 to 6 carbon atoms having halogen atom substituents, an alkenyl group of 3 to 5 carbon atoms or an alkynyl group of 3 to 5 carbon atoms.

4. A process according to claim 3, wherein $R^1$ is an alkyl group of 1 to 6 carbon atoms having halogen atom substituents.

5. A process according to claim 4, wherein the halogen atom is a chlorine atom.

6. A process according to claim 5, wherein $R^1$ is a chloropropyl group.

7. A process for producing a $\Delta^2$-1,2,4-triazolin-5-one derivative represented by the general formula (I)

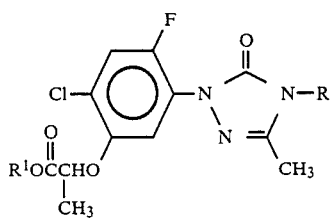
(I)

wherein R is a tetrafluoroethyl group and $R^1$ is a hydrogen atom, an alkyl group of 1 to 6 carbon atoms, an alkyl group of 1 to 6 carbon atoms having halogen atom substituents, a cycloalkyl group of 3 to 6 carbon atoms, a cycloalkyl group of 3 to 6 carbon atoms having halogen atom substituents, a cyanoalkyl group of 2 to 4 carbon atoms, an alkenyl group of 2 to 6 carbon atoms, an alkynyl group of 2 to 6 carbon atoms, an alkoxyalkyl group of 2 to 6 carbon atoms, an alkylthioalkyl group of 2 to 8 carbon atoms, an alkylsulfinylalkyl group of 2 to 6 carbon atoms, an alkylsulfonylalkyl group of 2 to 6 carbon atoms, an alkoxyalkoxyalkyl group of 3 to 8 carbon atoms, a hydroxycarbonylalkyl group of 2 to 3 carbon atoms, an alkoxycarbonylalkyl group of 3 to 6 carbon atoms, a benzyl group, a benzyl group having 1 to 2 substituents (selected from a halogen atom, an alkyl group of 1 to 3 carbon atoms, an alkoxy group of 1 to 3 carbon atoms, a nitro group, an alkoxycarbonyl group of 2 to 4 carbon atoms, a hydroxycarbonyl group and a phenoxy group), an alphamethylbenzyl group or a phenethyl group, characterized by chlorinating a compound represented by the general formula (II)

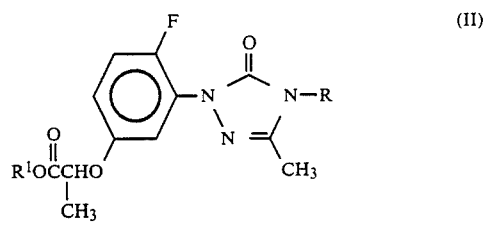

(wherein R and $R^1$ have each the same definition as given previously).

8. A process according to claim 7, wherein R is a 1,1,2,2-tetrafluoroethyl group and $R^1$ is a hydrogen atom, an alkyl group of 1 to 6 carbon atoms, an alkyl group of 1 to 6 carbon atoms having halogen atom substituents, an alkenyl group of 2 to 6 carbon atoms, an alkynyl group of 2 to 6 carbon atoms, an alkoxyalkyl group of 2 to 6 carbon atoms, an alkylthioalkyl group of 2 to 8 carbon atoms or an alkoxyalkoxyalkyl group of 3 to 8 carbon atoms.

9. A process according to claim 8, wherein R is a difluoromethyl group or a 1,1,2,2-tetrafluoroethyl group and $R^1$ is a hydrogen atom, an alkyl group of 1 to 6 carbon atoms, an alkyl group of 1 to 6 carbon atoms having halogen atom substituents, an alkenyl group of 3 to 5 carbon atoms or an alkynyl group of 3 to 5 carbon atoms.

10. A process according to claim 9, wherein $R^1$ is an alkyl group of 1 to 6 carbon atoms having halogen atom substituents.

11. A process according to claim 10, wherein the halogen atom is a chlorine atom.

12. A process according to claim 11, wherein $R^1$ is a chloropropyl group.

13. A process according to claim 9, wherein $R^1$ is a methyl group, an ethyl group, an n-propyl group or an isopropyl group.

14. A process according to claim 9, wherein $R^1$ is a 2-propenyl group.

15. A process according to claim 9, wherein $R^1$ is a 2-propynyl group.

* * * * *